(12) United States Patent
Kulkarni et al.

(10) Patent No.: US 8,916,194 B2
(45) Date of Patent: Dec. 23, 2014

(54) CONTROLLED RELEASE PHARMACEUTICAL COMPOSITIONS OF MILNACIPRAN

(75) Inventors: Shirishkumar Kulkarni, Pune (IN); Rajesh Kulkarni, Pune (IN); Pandharinath Jadhav, Pune (IN); Ashish Tiwari, Pune (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 13/819,415

(22) PCT Filed: Aug. 26, 2011

(86) PCT No.: PCT/IB2011/001955
§ 371 (c)(1),
(2), (4) Date: Feb. 27, 2013

(87) PCT Pub. No.: WO2012/028922
PCT Pub. Date: Mar. 8, 2012

(65) Prior Publication Data
US 2013/0156854 A1    Jun. 20, 2013

(30) Foreign Application Priority Data

Aug. 30, 2010 (IN) .............................. 972/KOL/2010

(51) Int. Cl.
| | | |
|---|---|---|
| *A61K 31/164* | (2006.01) | |
| *A61K 45/00* | (2006.01) | |
| *A61K 31/4178* | (2006.01) | |
| *A61K 31/165* | (2006.01) | |
| *A61K 9/20* | (2006.01) | |
| *A61K 45/06* | (2006.01) | |
| *A61K 9/28* | (2006.01) | |
| *A61K 9/24* | (2006.01) | |
| *A61K 31/439* | (2006.01) | |

(52) U.S. Cl.
CPC ............. *A61K 31/164* (2013.01); *A61K 31/165* (2013.01); *A61K 9/2095* (2013.01); *A61K 45/06* (2013.01); *A61K 9/2886* (2013.01); *A61K 9/2893* (2013.01); *A61K 31/4178* (2013.01); *A61K 9/209* (2013.01); *A61K 31/439* (2013.01); *A61K 45/00* (2013.01)
USPC ............................ 424/465; 514/397; 514/623

(58) Field of Classification Search
None
See application file for complete search history.

(56) References Cited

U.S. PATENT DOCUMENTS

| | | |
|---|---|---|
| 4,478,836 A | 10/1984 | Mouzin et al. |
| 6,210,714 B1 * | 4/2001 | Oshlack et al. ............... 424/476 |
| 6,602,911 B2 | 8/2003 | Kranzler et al. |
| 6,699,506 B1 | 3/2004 | Paillard et al. |
| 7,704,527 B2 | 4/2010 | Hirsh et al. |
| 8,263,125 B2 * | 9/2012 | Vaya et al. ..................... 424/469 |
| 2004/0132826 A1 | 7/2004 | Hirsh |
| 2006/0024366 A1 * | 2/2006 | Hirsh et al. .................. 424/468 |
| 2008/0131492 A1 * | 6/2008 | Nangia et al. ................ 424/449 |
| 2008/0200508 A1 * | 8/2008 | Rariy et al. ................... 514/321 |

FOREIGN PATENT DOCUMENTS

| | | |
|---|---|---|
| WO | 2006088305 A1 | 8/2006 |
| WO | 2006132307 | 12/2006 |

OTHER PUBLICATIONS

Puech et al. Milnacipran, a New Serotonin and Noradrenaline Reuptake Inhibitor: an Overview of its Antidepressant Activity and Clinical Tolerability; International Clinical Psychopharmacology. Mar. 1997.12: 99-108.

* cited by examiner

*Primary Examiner* — Robert A Wax
*Assistant Examiner* — Danah Al-Awadi
(74) *Attorney, Agent, or Firm* — The Webb Law Firm

(57) ABSTRACT

A controlled release pharmaceutical compositions comprising Milnacipran or pharmaceutically acceptable salts thereof is provided. The pharmaceutical composition comprises an immediate release core comprising Milnacipran or pharmaceutically acceptable salts thereof, pharmaceutically acceptable excipients and a coating on the immediate release core comprising rate controlling agents.

9 Claims, 2 Drawing Sheets

CONTROLLED RELEASE PHARMACEUTICAL COMPOSITIONS OF MILNACIPRAN

FIELD OF THE INVENTION

The present invention relates to controlled release pharmaceutical compositions comprising Milnacipran or pharmaceutically acceptable salts thereof.

BACKGROUND OF THE INVENTION

Milnacipran (cis-2-amino methyl-N, N-diethyl-1-phenyl cyclopropane carboxamide) is a psychoactive drug, which is a selective norepinephrine and serotonin reuptake inhibitor. It is used for the treatment of clinical depression and chronic pain especially fibromyalgia.

Milnacipran was first disclosed in U.S. Pat. No. 4,478,836. It is currently available as Savella® immediate release tablets in USA and is indicated for the management of fibromyalgia.

Milnacipran has demonstrated numerous adverse reactions in human clinical trials with tolerability decreasing with increasing dose (Puech A. et al., 1997, Int. Clin. Psychopharm, 12:99-108). Milnacipran may induce a locally mediated nausea via gastric irritation and the rapid onset of nausea was observed even prior to achieving peak plasma levels. An immediate release formulation of Milnacipran would not be suitable for a once-daily dosing regimen for treatment of depression and other related diseases due to Milnacipran's relatively short, half-life, which is 8 hours approximately.

Moreover, the currently available immediate release formulation of Milnacipran is not ideal for the treatment of health conditions that require Milnacipran doses equal or above 100 mg/day given either as once a day or twice a day due to high incidence of treatment-emergent side effects that leads to poor patient tolerance. Higher doses are required in the treatment of severe depression and other associated disorders. Milnacipran dosing regime of 100-250 mg daily was recently reported for the treatment of fibromyalgia (U.S. Pat. No. 6,602,911). It would be very difficult to reach the upper limits of the dose range using the currently available formulation due to the dose related treatment, emergent side effects and the need to titrate over a long period to reach the required dose.

Various approaches have been tried to develop controlled release pharmaceutical compositions of Milnacipran in order to lower the incidence and intensity of side effects, especially for higher dosages, and to lower or reduce the frequency of dosing.

U.S. Pat. No. 6,699,506 discloses a pharmaceutical composition with prolonged release, for oral administration of a single daily dose ranging from 60 to 140 mg of Milnacipran, having a multi-particulate form containing a plurality of microgranules each comprising an active microsphere containing a saccharose and/or starch nucleus of a size between 200 and 2000 µm and containing 150 to 1000 µm of Milnacipran and a binding agent, each microgranule being coated with a film having a base of at least one polymer insoluble in water but permeable to physiological liquids.

WO 2006/132307 provides a stabilized Milnacipran-containing composition in which Milnacipran or a salt thereof is allowed to exist in a porous carrier, packing a powder containing Milnacipran or a salt thereof in an HPMC capsule, or combining an additive which does not cause an interaction with Milnacipran with time.

WO 2006/088305 discloses a gastric-retentive controlled release mono-matrix tablet composition, comprising: a) at least one pharmacologically active substance; b) hydrogel-forming materials consisting of polyethylene oxide and at least one component selected from poloxamers and colloidal silica; and c) a carbon dioxide-generating material. The composition of the above application floats in gastric juice and can continuously release the active substance in the stomach at a constant rate for at least 2 hours.

U.S. Pat. No. 7,704,527 describes once daily Milnacipran modified release composition wherein release profile is characterized by a 0.05 to 4 hour lag time period during which less than 10% of the total Milnacipran dose is released into the stomach followed by a slow or extended release of the remaining drug within the intestine over a defined period of time. This patent discloses Milnacipran formulation comprising an extended release core of Milnacipran with one or more extended release excipient and a coating around the extended release core comprising a delayed release excipient.

US 2004/0132826 and US 2006/0024366 provide an extended release dosage unit of Milnacipran (optionally containing the immediate release portion) coated with delayed release coating. The Milnacipran composition, when administered orally, first passes through the stomach releasing from zero to less than 10% of the total Milnacipran dose and then enters the intestine where the drug is slowly released over an extended period of time.

There, still exists a need to develop controlled release pharmaceutical compositions comprising Milnacipran or pharmaceutically acceptable salts thereof that can provide alternative pharmacokinetic profiles in order to achieve the desired therapeutic effect and simultaneously eliminate or reduce the unwanted side effects.

Additionally there is a need to provide controlled release pharmaceutical compositions comprising Milnacipran or pharmaceutically acceptable salts thereof, wherein the composition provides release of at least 90% of Milnacipran between 8 to 20 hrs in vitro.

Thus the present invention provides controlled release pharmaceutical compositions comprising Milnacipran or pharmaceutically acceptable salts thereof, to control release of Milnacipran over prolonged period of time.

SUMMARY OF THE INVENTION

In accordance, one embodiment discloses controlled release pharmaceutical compositions comprising Milnacipran or pharmaceutically acceptable salts thereof comprising an immediate release core comprising Milnacipran or pharmaceutically acceptable salts thereof, pharmaceutically acceptable excipients and a coating on the immediate release core which comprises rate controlling agents.

Another embodiment discloses controlled release pharmaceutical compositions comprising Milnacipran or pharmaceutically acceptable salts thereof comprising an immediate release core comprising Milnacipran or pharmaceutically acceptable salts thereof and pharmaceutically acceptable excipients and a coating on the immediate release core which comprises rate controlling agents and optionally antiemetic drug selected from Dolasetron, Granisetron, Ondansetron, Tropisetron or Palonosetron.

Another embodiment discloses controlled release pharmaceutical compositions comprising Milnacipran or pharmaceutically acceptable salts thereof comprising an immediate release core comprising Milnacipran or pharmaceutically acceptable salts thereof, and optionally antiemetic drug selected from Dolasetron, Granisetron, Ondansetron, Tropisetron or Palonosetron and pharmaceutically acceptable excipients and a coating on the immediate release core which comprises rate controlling agents.

Yet another embodiment discloses controlled release pharmaceutical compositions comprising Milnacipran or pharmaceutically acceptable salts thereof comprising an immediate release core comprising Milnacipran or pharmaceutically acceptable salts thereof, pharmaceutically acceptable excipients and a coating on the immediate release core which comprises polymers which are water insoluble but semi permeable or permeable to physiological fluid.

Yet another embodiment provides controlled release pharmaceutical compositions comprising Milnacipran or pharmaceutically acceptable salts thereof adapted to release Milnacipran at predetermined time period, at least for about 14 hours.

Yet another embodiment discloses controlled release pharmaceutical compositions of Milnacipran or pharmaceutically acceptable salts thereof wherein the release of at least 90% of the total amount of Milnacipran is between 8 to 20 hours, preferably between 8 to 12 hours.

Yet another embodiment discloses controlled release pharmaceutical compositions of Milnacipran or pharmaceutically acceptable salts thereof wherein pharmaceutical compositions release at least 90% of Milnacipran in 12 hrs.

Yet another embodiment provides controlled release pharmaceutical compositions of Milnacipran or pharmaceutically acceptable salts thereof, which exhibits a mean $C_{max}$ in the range from about 50 ng/ml to about 500 ng/ml in the fed condition.

DETAILED DESCRIPTION OF THE INVENTION

Figure 1:
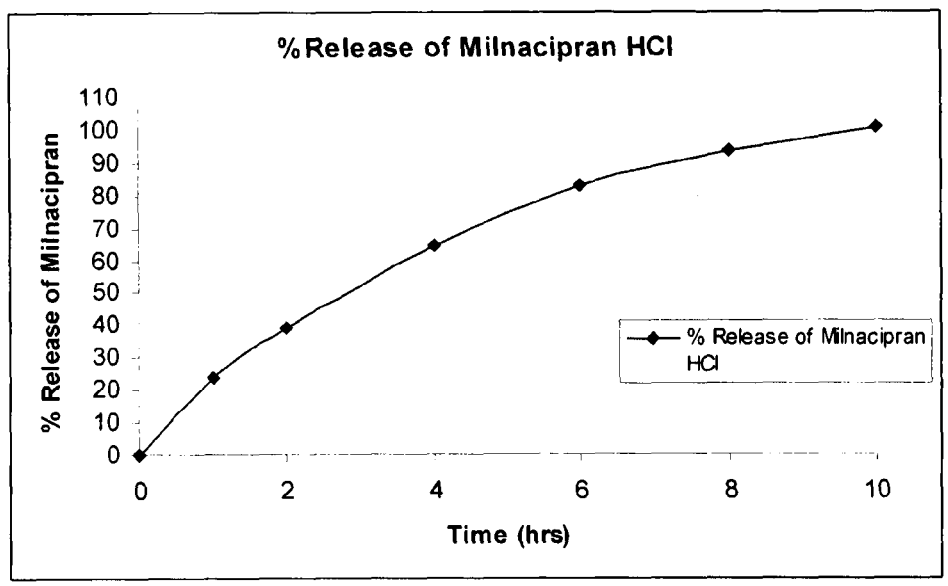
FIG. 1: shows a release profile of controlled release composition of example 1, in 900 ml 0.1 N HCl, USP apparatus Type I (Basket) at 100 rpm for 10 hrs.

The invention provides controlled release pharmaceutical compositions comprising Milnacipran or pharmaceutically acceptable salts which can deliver Milnacipran in a controlled manner over a period or extended period of time.

An embodiment discloses controlled release pharmaceutical compositions comprising Milnacipran or pharmaceutically acceptable salts thereof comprising an immediate release core comprising Milnacipran or pharmaceutically acceptable salts thereof, pharmaceutically acceptable excipients and a coating on the immediate release core which comprises rate controlling agents.

Another embodiment provides controlled release pharmaceutical compositions comprising Milnacipran or pharmaceutically acceptable salts thereof wherein the core comprises Milnacipran or pharmaceutically acceptable salts thereof and pharmaceutically acceptable excipients and a coating on the core which comprises rate controlling agents and optionally antiemetic drug selected from the group consisting of Dolasetron, Granisetron, Ondansetron, Tropisetron and Palonosetron.

Another embodiment discloses controlled release pharmaceutical compositions comprising Milnacipran or pharmaceutically acceptable salts thereof comprising an immediate release core comprising Milnacipran or pharmaceutically acceptable salts thereof, and optionally antiemetic drug selected from Dolasetron, Granisetron, Ondansetron, Tropisetron or Palonosetron and pharmaceutically acceptable excipients and a coating on the immediate release core which comprises rate controlling agents.

Another embodiment is further directed to controlled release pharmaceutical compositions comprising Milnacipran or pharmaceutically acceptable salts thereof, which releases at least 90% of Milnacipran between 8 to 20 hours. In a preferred embodiment, controlled release pharmaceutical compositions comprising Milnacipran or pharmaceutically acceptable salts thereof which releases at least 90% of Milnacipran between 8 to 12 hours.

As used herein "Milnacipran" also encompasses both individual enantiomer of Milnacipran (dextrogyral and levrogyral enantiomers) and their pharmaceutically acceptable salts, mixtures of Milnacipran enantiomers and their pharmaceutically acceptable salts, and active metabolites of Milnacipran and their pharmaceutically acceptable salts, unless otherwise noted.

As used herein, "pharmaceutically acceptable salts" refer to derivatives of Milnacipran wherein the Milnacipran is modified by making acid-addition or base-addition salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, methanesulfonic, ethane disulfonic, oxalic, isethionic and the like. The most preferable salt is hydrochloric salt.

The amount of Milnacipran or pharmaceutically acceptable salts thereof to be used ranges from about 25 to about 500 mg.

The term "immediate release core" used herein refers to a core composition comprising Milnacipran or pharmaceutically acceptable salts thereof devoid of any rate controlling agent.

The "immediate release core" releases more than 80% Milnacipran in 45 minutes when subjected to dissolution in 900 ml of 0.1N HCl using USP apparatus Type I (Basket) at 100 rpm.

The term "controlled release pharmaceutical compositions" herein refers to any composition which comprises Milnacipran, which is formulated to provide a gradual release of Milnacipran over a relatively longer period of time so that the concentration of Milnacipran is maintained in the blood for a longer time at a more uniform concentration than a corresponding immediate release composition comprising the same drug in the same amount. Controlled release pharmaceutical compositions mean any pharmaceutical composition which is other than immediate release pharmaceutical composition or is exchangeable with for example, extended release, sustained release, delayed release, or pulsed-release at a particular time.

The rate controlling agents may be polymers which are insoluble in water but semi permeable or permeable to physiological fluids. The rate controlling agents are selected from hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the trade name Eudragit® including Eudragit® L30D-55 and L100-55, Eudragit® L-10, Eudragit® S and Eudragit® NE, RL and RS, vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose, guar gum; zein or shellac or combinations thereof.

The amount of rate controlling agents may be readily determined by those skilled in the art in accordance with the desired release profile of the compositions. Preferably amount of rate controlling agents is in the range from about 2% to about 30% by weight of immediate release core.

The rate controlling agents can be used as aqueous or non aqueous dispersion or solution. Solvent such as dichloromethane, ethyl acetate, isopropyl alcohol, methanol, ethanol or a mixture of these solvents can be used to make non aqueous dispersion or solution of rate controlling agents.

The dispersion of rate controlling agents further includes conventional additives, such as pore formers, plasticizers, pigments, colorants, stabilizing agents, glidants etc. A pore former is a substance capable of promoting the creation of pores in the coating. Examples of pore formers include low-molecular weight cellulose derivatives which are soluble in water, polyvinylpyrrolidone, low-molecular weight polyethylene glycols, surfactants or any other soluble substances capable of creating pores in the coating and present in coating solution in amounts of between about 1 wt % and 20 wt % of the coating solution. A plasticizer is normally present to reduce the fragility of the coating, and will generally represent about 1 wt. % to about 50 wt. % relative to the dry weight of the polymer. Examples of typical plasticizers include polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during coating formation and drying, and will generally represent about 25 wt. % to about 100 wt. % of the polymer weight in the coating solution. One effective glidant is talc. Other glidants such as magnesium stearate and glycerol monostearate may also be used. Pigments such as titanium dioxide may also be used. Small quantities of an anti-foaming agent, such as a silicone (e.g., simethicone), may also be added to the coating composition.

Other pharmaceutically acceptable excipients include, but are not limited to, diluents, binders, lubricants and glidants known to person skilled in the art.

Diluents include, but are not limited to lactose, fructose, dextrose, sucrose, maltose, microcrystalline cellulose, starch, calcium hydrogen phosphate, Polyethylene glycol, mannitol and the like.

Binders include, but are not limited to starch, polyvinylpyrrolidone, sugars, gums, low molecular weight hydroxypropyl methylcellulose, hydroxypropyl cellulose, hydroxyethyl cellulose or the like.

Lubricants include, but are not limited to talc, magnesium stearate, calcium stearate, stearic acid, sodium stearyl fumarate, sodium benzoate or the like.

Glidants include, but are not limited to colloidal silicon dioxide, talc or the like.

The term "controlled release pharmaceutical compositions" includes a solid oral pharmaceutical composition that encompasses one or more individual immediate release units which are further coated with a rate controlling agent. The individual immediate release units may be in form of granules, pellets, minitablets, beads or tablet. Alternatively, the coated immediate release units can be filled into the capsule.

Controlled release pharmaceutical compositions may be prepared by any conventional techniques, not limited to, dry granulation, direct compression, wet granulation, and extrusion-spheronization, compression coating.

The controlled release pharmaceutical compositions may be administered adjunctively with antiemetic drugs such as Dolasetron, Granisetron, Ondansetron, Tropisetron and Palonosetron. In a preferred embodiment, controlled release pharmaceutical compositions are administered with Ondansetron.

By adjunctive administration is meant simultaneous administration of Milnacipran with antiemetic drugs in a same dosage forms such as tablet or capsule.

A tablet comprising controlled release pharmaceutical composition of Milnacipran and antiemetic drug may be a bilayer tablet. An immediate release composition of antiemetic drug can be added to the controlled release pharmaceutical composition of Milnacipran by various methods. These methods include such as coating of an immediate release composition of antiemetic drug on top of the controlled release core, by compression coating technique. Alternatively, granules of antiemetic drug can be compressed with coated units of Milnacipran in form of a bilayer tablet. A capsule may contain multiple units of controlled release pharmaceutical composition of Milnacipran and immediate release units of antiemetic drug. Alternatively, immediate release core of Milnacipran or pharmaceutically acceptable salts thereof may comprise Ondansetron, which is further coated with suitable rate controlling agents.

The present invention will be further understood by reference to the following non-limiting examples:

EXAMPLE 1 & EXAMPLE 2

| Sr. No. | Ingredients | Example 1 % W/W | Example 2 % W/W |
|---|---|---|---|
| Intragranular | | | |
| 1 | Milnacipran HCl | 5-25 | 5-25 |
| 2 | Microcrystalline Cellulose (MCC PH 101) | 10-30 | 10-30 |
| 3 | Polyethylene Glycol 3350 | 5-15 | 5-15 |
| 4 | Fructose | 20-45 | 20-45 |
| 5 | Mannitol 160 | 10-30 | 10-30 |
| 6 | PVP K30 | 2-8 | 2-8 |
| 7 | Acetone:IPA (95:5) | Qs | Qs |
| Extragranular | | | |
| 8 | Aerosil | 1-3 | 1-3 |
| 9 | Magnesium stearate | 1-3 | 1-3 |

-continued

| Sr. No. | Ingredients | Example 1 % W/W | Example 2 % W/W |
|---|---|---|---|
| | Weight of Core Tablet | | |
| | Functional Coating | | |
| 10 | Cellulose Acetate | 2-5 | 2-5 |
| 11 | Polyethylene Glycol 400 | 1-5 | 0.5-1.5 |
| 12 | Sodium Lauryl Sulfate | 1-5 | 0.5-1.5 |
| 13 | Isopropyl Alcohol | Q.S. | Q.S. |
| 14 | Dichloromethane | Q.S. | Q.S. |
| | Weight of functional coated tablet | | |
| | Color Coating | | |
| 15 | Opadry Yellow* | 1-3 | 1-3 |
| 16 | Isopropyl Alcohol | Q.S. | Q.S. |
| 17 | Dichloromethane | Q.S. | Q.S. |
| | Weight of Color coated Tablet | 1045.00 | 1045.00 |

*Composition of Opadry Yellow

| Sr. No. | Ingredients |
|---|---|
| 1 | HPMC 2910/Hypromellose 6 cp USP |
| 2 | HPMC 2910/Hypromellose 15 cp USP |
| 3 | Hydroxy Propyl Cellulose NF |
| 4 | Titanium Dioxide USP |
| 5 | Talc USP |
| 6 | Polyethylene Glycol 3350 |
| 7 | Colloidal Anhydrous Silica |
| 8 | Polysorbate 80 |

Brief Manufacturing Procedure:
I. Immediate Release Core of Milnacipran
  1. Weight all ingredients.
  2. Pass fructose & Milnacipran HCl through 60#.
  3. Pass Microcrystalline Cellulose, Polyethylene Glycol & Mannitol through 40#.
  4. Mix above sifted Milnacipran HCl, Microcrystalline Cellulose, Polyethylene Glycol, fructose & Mannitol.
  5. Dissolve PVP in Acetone & Isopropyl Alcohol.
  6. Granulate above blend of step 4 with binder solution of step 5 till desired end point.
  7. Keep granules in tray drier for drying at temperature 45° C.
  8. Sift dried granules through 25#.
  9. Lubricate sized granules with Aerosil & Magnesium Stearate.
  10. Compress above blend with 13.3 mm round punch plain on both sides.
II. Functional Coating:
Procedure:
  1. Disperse Sodium Lauryl sulfate in Isopropyl alcohol under stirring & continue stirring for 30 minutes.
  2. Add Dichloromethane to above dispersion and then add Cellulose acetate under stirring & continue stirring for 30 minutes.
  3. Finally add Polyethylene Glycol 400 to above solution of step 2 under stirring & continue stirring for 30 minutes.
  4. Coat compressed tablets using above coating solution in suitable coating machine.
III. Color Coating:
Procedure:
  1. Add Opadry Yellow to Isopropyl alcohol & Dichloromethane mixture under stirring & continue stirring for 30 minutes.
  2. Coat functional coated tablets using above colour coating solution in suitable coating machine.

EXAMPLE 3

Milnacipran tablets, prepared as per example 2 are further coated with the following Ondansetron composition.

| | Ondansetron Coating | |
|---|---|---|
| 15 | Ondansetron Hydrochloride Dihydrate | 0.5-2.0 |
| 16 | Opadry Clear** | 0.5-2.0 |
| 17 | Methanol | Qs |
| 18 | Water | Qs |
| Weight of Ondansetron Coated Tablet | | |
| | Color Coating | |
| 19 | Opadry Pink*** | 1-3 |
| 20 | Isopropyl Alcohol | Q.S. |
| 21 | Dichloromethane | Q.S. |
| Weight of Color coated tablet | | 1055.00 |

**Composition of Opadry Clear: Hypromellose & Polyethylene Glycol
***Composition of Opadry Pink

| Sr. No. | Ingredients |
|---|---|
| 1 | HPMC 2910/Hypromellose 6 cp USP |
| 2 | Titanium Dioxide USP |
| 3 | Propylene Glycol |
| 4 | Macrogol/PEG 6000 NF |
| 5 | Talc USP |

Ondansetron Coating:
Brief Manufacturing Procedure:
  1. Dissolve Ondansetron Hydrochloride Dihydrate in Methanol & Water mixture.
  2. Add Opadry Clear to above solution, under stirring till to get clear solution.
  3. Coat compressed tablets of example 2 using above coating solution in suitable coating machine.
  4. Tablets of step 3 are further coated with suitable color coating.
Color Coating:
Procedure:
  1. Add Opadry Pink to Isopropyl alcohol & Dichloromethane mixture under stirring & continue stirring for 30 minutes.
  2. Coat above coated tablets using above colour coating solution in suitable coating machine.

Figure 2:
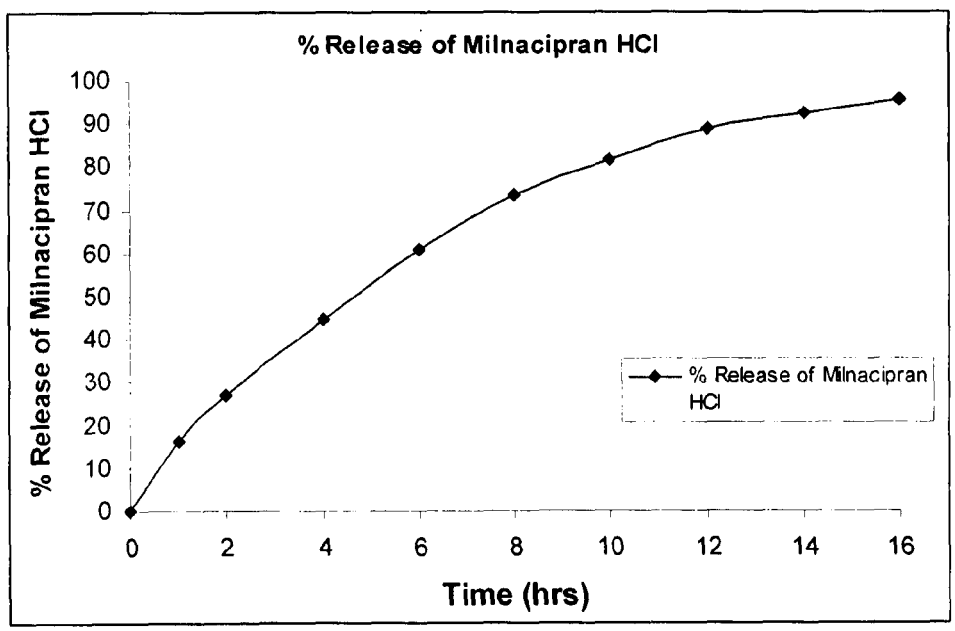
FIG. 2: shows a release profile of controlled release composition of example 2, in 900 ml 0.1 N HCl, USP apparatus Type I (Basket) at 100 rpm for 16 hrs.
Figure 3:
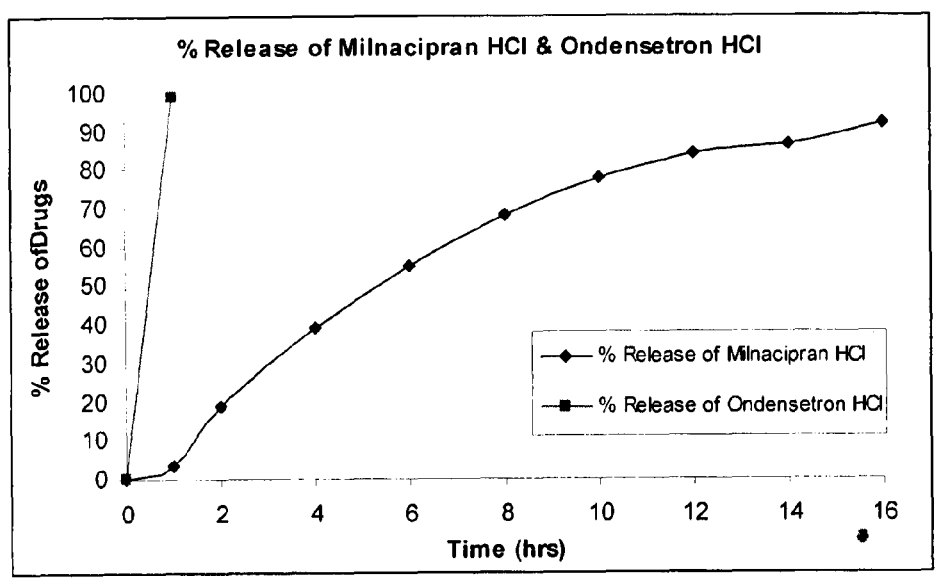
FIG. 3: shows a release profile of controlled release composition of example 3, in 900 ml 0.1 N HCl, USP apparatus Type I (Basket) at 100 rpm for 16 hrs.

The result of in-vitro dissolution of pharmaceutical compositions of examples 1-3 are shown in FIG. 1-3 respectively.

The invention claimed is:
1. A controlled release pharmaceutical composition comprising (i) an immediate release core consisting of Milnacipran or a pharmaceutically acceptable salt thereof, and one or more pharmaceutically acceptable excipients, wherein the immediate release core is free of rate controlling agents and (ii) a coating comprising a rate controlling agent on the immediate release core.
2. The controlled release pharmaceutical composition of claim 1, wherein the rate controlling agent is water insoluble but semi permeable or permeable to physiological fluids.
3. The controlled release pharmaceutical composition of claim 2, wherein the rate controlling agent is selected from hydroxypropyl methyl cellulose acetate succinate, hydroxy propyl methylcellulose phthalate, methylcellulose, ethylcellulose, cellulose acetate, cellulose acetate phthalate, cellulose acetate trimellitate, carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins; vinyl polymers and copolymers such as polyvinyl pyrrolidone, vinyl acetate, vinylacetate phthalate, vinyl acetate crotonic acid copolymer, ethylene-vinyl acetate copolymer; enzymatically degradable polymers such as azo polymers, pectin, chitosan, amylase, guar gum, zein, shellac or a combination thereof.

4. The controlled release pharmaceutical composition of claim 1, wherein the pharmaceutically acceptable excipient is selected from a diluent, a binder, a lubricant, or a glidant.

5. The controlled release pharmaceutical composition of claim 1, wherein the composition releases at least 90% of Milnacipran between 8 to 20 hours, when dissolution is carried out in 900 ml of 0.1 N HCl, USP apparatus Type I (Basket) at 100 RPM.

6. The controlled release pharmaceutical composition of claim 5, wherein the pharmaceutical composition releases at least 90% of Milnacipran in 12 hours.

7. The controlled release pharmaceutical composition of claim 1, wherein Milnacipran or pharmaceutically acceptable salt thereof is Milnacipran Hydrochloride.

8. The controlled release pharmaceutical composition of claim 1, further comprising an antiemetic drug coated onto the coating comprising the rate controlling agent.

9. The controlled release pharmaceutical composition of claim 8, wherein the antiemetic drug is selected from Dolasetron, Granisetron, Ondansetron, Tropisetron and Palonosetron.

* * * * *